United States Patent
Shi et al.

(10) Patent No.: US 10,821,149 B2
(45) Date of Patent: Nov. 3, 2020

(54) COMPOSITION AND THE USE THEREOF

(71) Applicant: INFINITUS (CHINA) COMPANY LTD., Jiang Men, Guangdong (CN)

(72) Inventors: Bin Shi, Jiang Men (CN); Xiaolei Guo, Jiang Men (CN); Chung Wah Ma, Jiang Men (CN); Chuixin Qin, Jiang Men (CN); Zhen Luo, Jiang Men (CN); Wei Zhang, Jiang Men (CN)

(73) Assignee: INFINITUS (CHINA) COMPANY LTD., Jiang Men, Guangdong (CN)

( * ) Notice: Subject to any disclaimer, the term of this patent is extended or adjusted under 35 U.S.C. 154(b) by 662 days.

(21) Appl. No.: 15/175,778

(22) Filed: Jun. 7, 2016

(65) Prior Publication Data

US 2017/0014467 A1 Jan. 19, 2017

(30) Foreign Application Priority Data

Jul. 14, 2015 (CN) .......................... 2015 1 0412685

(51) Int. Cl.
| | |
|---|---|
| *A61K 36/8994* | (2006.01) |
| *A61K 36/896* | (2006.01) |
| *A61K 36/28* | (2006.01) |
| *A61K 36/88* | (2006.01) |
| *A61K 36/884* | (2006.01) |
| *A61K 36/488* | (2006.01) |
| *A23L 33/105* | (2016.01) |
| *A61K 36/68* | (2006.01) |
| *A61K 36/90* | (2006.01) |

(52) U.S. Cl.
CPC ........ *A61K 36/8994* (2013.01); *A23L 33/105* (2016.08); *A61K 36/28* (2013.01); *A61K 36/488* (2013.01); *A61K 36/68* (2013.01); *A61K 36/88* (2013.01); *A61K 36/884* (2013.01); *A61K 36/896* (2013.01); *A61K 36/90* (2013.01)

(58) Field of Classification Search
CPC .. A61K 36/8994; A61K 36/28; A61K 36/488; A61K 36/68; A61K 36/896; A61K 36/90
See application file for complete search history.

(56) References Cited

FOREIGN PATENT DOCUMENTS

| | | | |
|---|---|---|---|
| CN | 1943741 A | * 4/2007 | |
| CN | 103100006 A | * 5/2013 | ............. A61K 36/90 |
| HU | 2013000497 A1 | * 3/2015 | |

OTHER PUBLICATIONS

Lee et al. J Liq Chromatogr Relat Technol. 36(4):513-524 (Year: 2013).*
McLaughlin, A. "Food that is good for eczema". Internet Archive: Oct. 30, 2011 [Internet Archive Date: Nov. 17, 2018]. Retrieved from: < URL: https://web.archive.org/web/20111030022819/https://www.livestrong.com/article/345886-food-that-is-good-for-eczema/>.2 pages (Year: 2010).*
Swierzewski, et al. Gout & Natural Treatment, Diet: Naturopathic Treatment/Diet for Gout. In healthcommunities.com [online]. Web archive date: May 26, 2011 [retrieved on Jun. 21, 2019]. Retrieved from the Internet: <URL: http://www.healthcommunities.com/gout/natural-medicine.shtml> (Year: 2000).*
Renbin et al. Journal of Traditional Chinese Medicine 94; 28(2): 94-97 (Year: 2008).*

* cited by examiner

*Primary Examiner* — Amy L Clark
(74) *Attorney, Agent, or Firm* — Yue (Robert) Xu; Apex Attorneys at Law, LLP

(57) ABSTRACT

The present invention relates to the pharmaceutical field, particularly to a composition and the use thereof. The composition serves to lower uric acid through the combination of several traditional Chinese medicines of *Smilacis glabra rhizoma, Cichorii herba, Plantaginis herba* and *Coicis* semen. On the basis of the combination of the traditional Chinese medicines described above, the addition of *Alismatis rhizoma* is able to improve the effect of lowering uric acid more significantly. Further, on the basis of the combination of the traditional Chinese medicines described above, the addition of tuna was able to improve the effect of lowering uric acid more significantly. A comprehensive analysis of the experimental results described above indicates that the compositions provided in the present invention have a significant effect of lowering uric acid.

2 Claims, No Drawings

COMPOSITION AND THE USE THEREOF

CROSS REFERENCE OF RELATED APPLICATIONS

The present application claims the priority of Chinese Patent Application No. 201510412685.5, as filed on Jul. 14, 2015 and titled with "Composition and use thereof", and the disclosure of which is incorporated herein by reference.

FIELD

The present invention relates to the pharmaceutical field, particularly to a composition and the use thereof.

BACKGROUND

Hyperuricemia is a metabolic disease caused by the increase of serum uric acid due to the disorder of purine metabolite of human, and the production and excretion of uric acid is about to be equal daily, with one-third generate from food and two-thirds synthesized by the body itself, and with respect to excretion pathways, one-third of the amount excreted by the intestine and two-thirds by the kidneys. Problems in any aspect of the various ways aforementioned will result in an increase of uric acid. Rising of uric acid may hinder the process of uric acid secretion by the blood, thus making it unable to be discharged. Excessively high content of serum uric acid may also induce other diseases, such as arthritis, hyperuricemia, kidney stones etc.

Traditional Chinese medical science believes that hyperuricemia results from congenital insufficiency of kidney-qi or gradual disappearance of positive-qi which weaken the function of gasifying and excreting the aqueous liquid, and from excessive intake of fatness, sweetness and intensive tastes which hurt the spleen and stomach, causing disorders of moisture transport, retention of wet and turbid pathogen that is heavy, turbid, greasy and stagnant in the organs, impediment of qi activity, resulting in the disorder of the rise and fall of qi activity, unfavorable excretion of urine and turbid-qi, stagnancy of turbid-qi and blood stasis in the channels and joints, incorporation of moisture and turbid-qi, and blocked circulation of qi and blood, thus inducing the generation of phlegm, moisture and blood stasis. The impediment of blood circulation and the stagnancy of condensed moisture in turn aggravate the generation of phlegm, moisture and blood stasis. The key factor of the impediment of the channels and vessels by phlegm, moisture and blood stasis lies mainly in the excess of pathogen and the deficiency of resistance. Based on this, the treatment should be focused on "strengthening the spleen, unblocking the channels, eliminating dampness and excreting turbid-qi".

As modern studies suggest, currently 90 percent of hyperuricemia is caused by the disorder of uric acid excretion, which in the kidney mainly includes four processes: the filtration by glomerulus, the reabsorption by renal tubule and collecting tubule, and the secretion and reabsorption after secretion by renal tubule and collecting tubule, with the corresponding proteins involved in the completion of each process except the filtration by glomerulus, and only 8% to 12% of the uric acid eventually excreted out of body. At the level of genes, it has currently been found that the genes involved in the absorption and secretion of uric acid include dozens of genes encompassing urate anion transporter 1 (URAT1), fructose transporter 9 (GLUTS), organic anion transporters (OATs family), urate transporter (UAT) and the like. The abnormal expressions of each protein involved in uric acid transportation may possibly lead to hyperuricemia.

Accordingly, it is of important practical significance to provide a composition that having uric acid-lowering effect.

SUMMARY

In view of this, the present invention provides a composition and the use thereof. The composition provides an uric acid-lowering effect through the combination of several traditional Chinese medicines of *Smilacis glabrae rhizoma*, *Cichorii herba*, *Plantaginis herba* and *Coicis* semen. On the basis of the combination of the traditional Chinese medicines described above, the addition of *Alismatis rhizoma* is able to enhance the uric acid-lowering effect more significantly. Further, on the basis of the combination of the traditional Chinese medicines described above, the addition of tuna is able to improve the uric acid-lowering effect more significantly.

To achieve the above object of the invention, the present invention provides the following technical solutions:

The present invention provides a composition comprising *Smilacis glabra rhizoma*, *Cichorii herba*, *Plantaginis herba* and *Coicis* semen.

Traditional Chinese medicine theory believes that "dampness cannot be eliminated without purgation". Therefore, the compositions of the present invention aid in the process of "strengthening the spleen", "eliminating dampness", and "clearing turbid-qi", and as a result, the healthy operation of the spleen-qi cut off the internal source of moisture and turbid-qi; and the elimination of dampness, the excretion of turbid-qi, and the unclogging of the two apertures in the front and back of the body enable the generated moisture and dampness to be purged through defecation, then since the pathogen finds an outlet, the heat pathogen is cleared by itself and the phlegm cannot be generated as the moisture is eliminated, and the manifestation and root cause of the disease are both cured.

In the present invention, *Smilacis glabrae rhizoma* is sweet, light and flat, and it goes to the liver and spleen channels, eliminates dampness, clears toxins, and unblocks the joints as a monarch drug; *Cichorii herba* is slightly bitter, salty and cool, and it clears the liver, benefits the gallbladder, strengthens the spleen, helps digestion, induces diuresis, and relieving edema; *Plantaginis herba* clears heat, induces diuresis, cools the blood and clears toxins, the two above are ministerial drugs in combination; *Coicis* semen induces diuresis, eliminates dampness, strengthens the spleen, antidiarrhea, and clears toxins as an adjuvant drug. The medicines described above used in combination act to strengthen the spleen, eliminate dampness, clear heat and unblock the joints. The addition of tuna extract containing peptides component to the composition enhances its uric acid-lowering effect significantly.

In some embodiments of the present invention, the composition of the present invention comprises the following components based on part by weight.

| | |
|---|---|
| Smilacis Glabra Rhizoma | 3 to 29 parts |
| Cichorii Herba | 3 to 16 parts |
| Plantaginis Herba | 3 to 16 parts |
| Coicis semen | 3 to 21 parts. |

In some embodiments of the present invention, the composition of the present invention also comprises *Alismatis rhizoma*.

In some embodiments of the present invention, the composition of the present invention comprises the following components based on part by weight,

| | |
|---|---|
| Smilacis Glabra Rhizoma | 3 to 29 parts |
| Cichorii Herba | 3 to 16 parts |
| Plantaginis Herba | 3 to 16 parts |
| Coicis semen | 3 to 21 parts |
| Alismatis Rhizoma | 1 to 10 parts. |

In some embodiments of the present invention, the composition of the present invention also comprises tuna.

In some embodiments of the present invention, the composition of the present invention comprises the following components based on part by weight,

| | |
|---|---|
| Smilacis Glabra Rhizoma | 3 to 29 parts |
| Cichorii Herba | 3 to 16 parts |
| Plantaginis Herba | 3 to 16 parts |
| Coicis semen | 3 to 21 parts |
| Tuna | 0.1 to 5 parts. |

In some embodiments of the present invention, the tuna could be the tissues and organs of tuna itself (including the fish skin, fish flesh, fish bones, fins, etc.), and also could be the extract of tuna. Among these, the tuna extract could be commercially purchased, and also could be prepared by oneself.

In some embodiments of the present invention, the preparation method of tuna extract comprises: taking and grinding the tuna, pretreatment, enzymatic hydrolysis, enzyme inactivation, centrifugation to obtain a supernatant, concentration and drying. As is preferred, the pre-treatment is heating at within 80 and 100° C. for 5 to 30 min. As is preferred, the temperature of the enzymatic hydrolysis is 50-60° C., and the time of the enzymatic hydrolysis is 3.0-9.0 h. As is preferred, protease is employed in the enzymatic hydrolysis. More preferably, the protease is selected from the group consisting of acidic protease, papain, pepsin, trypsin, proteolytic enzyme, neutral protease, flavourzyme and Alcalase protease, and the protease is used in an amount of 0.5% to 3.0% by weight of the pretreated tuna. As is preferred, the temperature of the enzyme inactivation is 90° C.-100° C., and the time of enzyme inactivation is 10-20 min. As is preferred, the concentration is performed under vacuum conditions of 0.03-0.08 MPa and 60-80° C. to a solid content of 30-45%.

In some embodiments of the present invention, the composition of the present invention comprises the following components based on part by weight,

| | |
|---|---|
| Smilacis Glabra Rhizoma | 3 to 29 parts |
| Cichorii Herba | 3 to 16 parts |
| Plantaginis Herba | 3 to 16 parts |
| Coicis semen | 3 to 21 parts |
| Alismatis Rhizoma | 1 to 10 parts |
| Tuna | 0.1 to 5 parts |

In some embodiments of the present invention, the composition of the present invention also comprises *Pueraia lobata radix*.

In some embodiments of the present invention, the composition of the present invention comprises the following components based on part by weight,

| | |
|---|---|
| Smilacis Glabra Rhizoma | 3 to 29 parts |
| Cichorii Herba | 3 to 16 parts |
| Plantaginis Herba | 3 to 16 parts |
| Coicis semen | 3 to 21 parts |
| Alismatis Rhizoma | 1 to 10 parts |
| Tuna | 0.1 to 5 parts |
| Pueraia Lobata Radix | 3 to 11 parts |

The present invention also provides the use of the described composition in the preparation of drugs, food and/or health products that lowering uric acid.

A variety of dosage forms in terms of pharmaceutics such as oral liquid, capsules, tablets, powders or granules and the like could be produced by conventional preparation process (such as water extraction or alcohol extraction, etc.) without limitations here.

In some embodiments of the present invention, the methods for the preparation of the described composition are also provided. The preparation methods could be direct mixing of the raw materials, and also could be processing.

The methods for the preparation of the described composition may include extracting the raw material described above for twice, with the addition of water in an amount of 12 times (by weight) at the first time which boiling extraction for 1.5 hours, and the addition of water in an amount of 8 times (by weight) at the second time which boiling extraction for 1 hour, combining the extracts of the above two extractions; filtering the obtained extract at the temperature of 65° C.-85° C. in the vacuum of between −0.03 and −0.08 Mpa, and concentrating to 20%-30% solids. The composition could also be canned after the addition of auxiliaries, thus obtaining pharmaceutical formulation, food or health-care products.

The composition of the present invention having the function of lowering uric acid could also be made into food, health-care products and drugs, the formulations of which are of oral liquid, capsules, tablets, pills, pulvis, powders or granules.

The present invention provides a composition and the use thereof. The composition serves to lowering uric acid through the combination of several traditional Chinese medicines of *Smilacis glabra rhizoma, Cichorii herba, Plantaginis herba* and *Coicis* semen. On the basis of the combination of the traditional Chinese medicines described above, the addition of *Alismatis rhizoma* is able to improve the uric acid-lowering effect more significantly. Further, on the basis of the combination of the traditional Chinese medicines described above, the addition of tuna is able to improve the effect of lowering uric acid more significantly. Furthermore, with the integration of the above experimental results, the compositions of the present invention have a significant effect of lowering uric acid.

DETAILED DESCRIPTION

The present invention discloses a composition and the use thereof, which could be implemented with suitable modifications of the process parameters by those skilled in the art in light of the present disclosure. It is of particular note that all the similar alterations and modifications are clear to those skilled in the art and deemed to be included in the present invention. Methods and applications of the present invention have been described by the preferred examples, and it is obvious that those in related art are able to make changes or appropriate alternations and the combinations thereof to the methods and applications described herein to implement and apply the inventive technology without departing from the disclosure, spirit and scope of the present invention.

The present invention provides a composition and the use thereof. The components and reagents are all commercially available. A variety of dosage forms in terms of pharmaceutics such as oral liquid, capsules, tablets, powders or granules and the like may be produced by conventional formulation process (such as water extraction or alcohol extraction, etc.) without limitations here.

The description of the disclosed examples enables those skilled in the art to implement or make use of the present invention. Various modifications to these examples will be apparent to those skilled in the art, and the general principles defined herein may be realized in other examples without departing from the spirit or scope of the present invention. Accordingly, the present invention will not be limited to these examples illustrated herein, but consistent with the widest range in accordance with the principles and novel features disclosed herein.

The present invention is further explained below in combination with the Examples:

Example 1 The Composition

It is obtained by weighing precisely and mixing 29 g of *Smilacis glabra rhizoma*, 9 g of *Cichorii herba*, 3 g of *Plantaginis herba* and 12 g of *Coicis* semen.

Example 2 The Composition

It is obtained by weighing precisely and mixing 3 g of *Smilacis glabra rhizoma*, 16 g of *Cichorii herba*, 9 g of *Plantaginis herba* and 21 g of *Coicis* semen.

Example 3 The Composition

It is obtained by weighing precisely and mixing 16 g of *Smilacis glabra rhizoma*, 3 g of *Cichorii herba*, 16 g of *Plantaginis herba* and 3 g of *Coicis* semen.

Example 4 The Composition

It is obtained by weighing precisely and mixing 29 g of *Smilacis glabra rhizoma*, 9 g of *Cichorii herba*, 3 g of *Plantaginis herba*, 12 g of *Coicis* semen and 1 g of *Alismatis rhizoma*.

Example 5 The Composition

It is obtained by weighing precisely and mixing 3 g of *Smilacis glabra rhizoma*, 16 g of *Cichorii herba*, 9 g of *Plantaginis herba*, 21 g of *Coicis* semen and 6 g of *Alismatis rhizoma*.

Example 6 The Composition

It is obtained by weighing precisely and mixing 16 g of *Smilacis glabra rhizoma*, 3 g of *Cichorii herba*, 16 g of *Plantaginis herba*, 3 g of *Coicis* semen and 10 g of *Alismatis rhizoma*.

Example 7 The Composition

It is obtained by weighing precisely and mixing 29 g of *Smilacis glabra rhizoma*, 9 g of *Cichorii herba*, 3 g of *Plantaginis herba*, 12 g of *Coicis* semen and 1 g of *Alismatis rhizoma*.

Example 8 The Composition

It is obtained by weighing precisely and mixing 3 g of *Smilacis glabra rhizoma*, 16 g of *Cichorii herba*, 9 g of *Plantaginis herba*, 21 g of *Coicis* semen and 6 g of *Alismatis rhizoma*.

Example 9 The Composition

It is obtained by weighing precisely and mixing 16 g of *Smilacis glabra rhizoma*, 3 g of *Cichorii herba*, 16 g of *Plantaginis herba*, 3 g of *Coicis* semen and 10 g of *Alismatis rhizoma*.

Example 10 The Composition

It is obtained by weighing precisely and mixing 29 g of *Smilacis glabra rhizoma*, 9 g of *Cichorii herba*, 3 g of *Plantaginis herba*, 12 g of *Coicis* semen, 1 g of *Alismatis rhizoma* and 2.5 parts of tuna.

Example 11 The Composition

It is obtained by weighing precisely and mixing 3 g of *Smilacis glabra rhizoma*, 16 g of *Cichorii herba*, 9 g of *Plantaginis herba*, 21 g of *Coicis* semen, 6 g of *Alismatis rhizoma* and 5 parts of tuna g.

Example 12 The Composition

It is obtained by weighing precisely and mixing 16 g of *Smilacis glabra rhizoma*, 3 g of *Cichorii herba*, 16 g of *Plantaginis herba*, 3 g of *Coicis* semen, 10 g of *Alismatis rhizoma* and 0.1 parts of tuna.

Example 13 The Composition 20 g of *Smilacis glabra rhizoma*, 15 g of *Cichorii herba*, 8 g of *Plantaginis herba*, 12 g of *Coicis semen*, 8 g of *Pueraia lobata radix*, 3 g of *Alismatis rhizoma* and 0.5 g of tuna extract were weighed precisely.

The method for the preparation of the tuna extract includes taking and grinding the tuna, heating for 30 min at 80° C. as pretreatment, and enzymatic hydrolyzing at the temperature of 50° C. for a duration of 7.0 h. Pepsin was employed in the enzymatic hydrolysis in an amount of 2.5% by weight of the pretreated tuna.

Next is the inactivation of the enzymes at the temperature of 90° C. for a duration of 13 min.

The supernatant was obtained by centrifugation, which was concentrated to a solids content of 30% at 0.03 MPa and 74° C. under vacuum and dried.

The raw materials described above were extracted twice, with the addition of water in an amount of 12 times at the first time, which was boiling extracted for 1.5 hours, and the addition of water in an amount of 8 times at the second time, which was boiling extracted for 1 hour, followed by the combination of the extracts from the above two extractions; the extracts were filtered at the temperature of 80° C. in a vacuum of −0.03 Mpa, and concentrated to a solids content of 24%; the oral liquid products were obtained by canning after the addition of auxiliaries.

Example 14

8 g of *Smilacis glabra rhizoma*, 15 g of *Cichorii herba*, 15 g of *Plantaginis herba*, 10 g of *Coicis* semen, 10 g of

*Pueraia lobata radix*, 4 g of *Alismatis rhizoma* and 4.0 g of tuna extract were weighed precisely.

The method for the preparation of the tuna extract includes taking and grinding the tuna, heating for 25 min at 100° C. as pretreatment, and enzymatic hydrolyzing at a temperature of 60° C. for a duration of 8.0 h. Trypsin was employed in the enzymatic hydrolysis in an amount of 2.0% by weight of the pretreated tuna.

Next was the inactivation of the enzymes at the temperature of 100° C. for a duration of 14 min.

The supernatant was obtained by centrifugation, which was concentrated to a solids content of 45% at 0.08 MPa and 66° C. under vacuum and dried.

The raw materials described above were extracted twice, with the addition of water in an amount of 12 times at the first time which was boiling extracted for 1.5 hours, and the addition of water in an amount of 8 times at the second time which was boiling extracted for 1 hour, followed by the combination of the extracts from the above two extractions; the extracts were filtered at the temperature of 81° C. in a vacuum of −0.08 Mpa, and concentrated to a solids content of 26%; the capsule products were obtained with the addition of auxiliaries according to the conventional process for producing capsules.

Example 15

20 g of *Smilacis glabra rhizoma*, 15 g of *Cichorii herba*, 13 g of *Plantaginis herba*, 10 g of *Coicis semen*, 8 g of *Pueraia lobata radix*, 3 g of *Alismatis rhizoma* and 0.4 g of tuna extract were weighed precisely.

The method for the preparation of the tuna extract includes taking and grinding the tuna, heating for 20 min at 90° C. as pretreatment, and enzymatic hydrolyzing at the temperature of 55° C. for a duration of 6.0 h. Proteolytic enzymes were employed in the enzymatic hydrolysis in an amount of 1.5% by weight of the pretreated tuna.

Next was the inactivation of the enzymes at the temperature of 95° C. for a duration of 16 min.

The supernatant was obtained by centrifugation, which is concentrated to a solids content of 35% at 0.05 MPa and 75° C. under vacuum and dried.

The raw materials described above were extracted twice, with the addition of water in an amount of 12 times at the first time, which was boiling extracted for 1.5 hours, and the addition of water in an amount of 8 times at the second time, which was boiling extracted for 1 hour, followed by the combination of the extracts from the above two extractions; the extracts were filtered at the temperature of 72° C. in a vacuum of −0.05 Mpa, and concentrated to a solids content of 28%; the tablet products were obtained with the addition of auxiliaries according to the conventional process for producing tablets.

Example 16

18 g of *Smilacis glabra rhizoma*, 13 g of *Cichorii herba*, 10 g of *Plantaginis herba*, 17 g of *Coicis semen*, 7 g of *Pueraia lobata radix*, 3 g of *Alismatis rhizoma* and 0.3 g of tuna extract were weighed precisely.

The method for the preparation of the tuna extract includes taking and grinding the tuna, heating for 15 min at 85° C. as pretreatment, and enzymatic hydrolyzing at the temperature of 52° C. for a duration of 4.0 h. Neutral protease was employed in the enzymatic hydrolysis in an amount of 1.0% by weight of the pretreated tuna.

Next was the inactivation of the enzymes at the temperature of 98° C. for a duration of 18 min.

The supernatant was obtained by centrifugation, which was concentrated to a solids content of 40% at 0.04 MPa and 65° C. under vacuum and dried.

The raw materials described above were extracted twice, with the addition of water in an amount of 12 times at the first time, which was boiling extracted for 1.5 hours, and the addition of water in an amount of 8 times at the second time which was boiling extracted for 1 hour, followed by the combination of the extracts from the above two extractions; the extracts were filtered at the temperature of 68° C. in a vacuum of −0.04 Mpa, and concentrated to a solids content of 22%; the pill products were obtained with the addition of auxiliaries according to the conventional process for producing pills.

Example 17

15 g of *Smilacis glabra rhizoma*, 10 g of *Cichorii herba*, 8 g of *Plantaginis herba*, 15 g of *Coicis semen*, 5 g of *Pueraia lobata radix*, 2 g of *Alismatis rhizoma* and 1.0 g of tuna extract were weighed precisely.

The method for the preparation of the tuna extract includes taking and grinding the tuna, heating for 10 min at 95° C. as pretreatment, and enzymatic hydrolyzing at the temperature of 58° C. for a duration of 5.0 h. Flavourzyme was employed in the enzymatic hydrolysis in an amount of 0.5% by weight of the pretreated tuna.

Next was the inactivation of the enzymes at the temperature of 92° C. for a duration of 12 min.

The supernatant was obtained by centrifugation, which was concentrated to a solids content of 36% at 0.06 MPa and 70° C. under vacuum and dried.

The raw materials described above were extracted twice, with the addition of water in an amount of 12 times at the first time, which was boiling extracted for 1.5 hours, and the addition of water in an amount of 8 times at the second time, which was boiling extracted for 1 hour, followed by the combination of the extracts from the above two extractions; the extracts were filtered at the temperature of 70° C. in a vacuum of −0.06 Mpa, and concentrated to a solids content of 25%; the pulvis products were obtained with the addition of auxiliaries according to the conventional process for producing pulvis.

Example 18

25 g of *Smilacis glabra rhizoma*, 12 g of *Cichorii herba*, 12 g of *Plantaginis herba*, 15 g of *Coicis semen*, 6 g of *Pueraia lobata radix*, 3 g of *Alismatis rhizoma* and 0.5 g of tuna extract were weighed precisely.

The method for the preparation of the tuna extract includes taking and grinding the tuna, heating for 5 min at 100° C. as pretreatment, and enzymatic hydrolyzing at the temperature of 56° C. for a duration of 9.0 h. Alcalase protease was employed in the enzymatic hydrolysis in an amount of 3.0% by weight of the pretreated tuna.

Next was the inactivation of the enzymes at the temperature of 94° C. for a duration of 10 min.

The supernatant was obtained by centrifugation, which was concentrated to a solids content of 42% at 0.07 MPa and 80° C. under vacuum and dried.

The raw materials described above were extracted twice, with the addition of water in an amount of 12 times at the first time which was boiling extracted for 1.5 hours, and the addition of water in an amount of 8 times at the second time, which was boiling extracted for 1 hour, followed by the combination of the extracts from the above two extractions; the extracts were filtered at the temperature of 65° C. in a vacuum of −0.07 Mpa, and concentrated to a solids content of 30%; the powder products were obtained with the addition of auxiliaries according to the conventional process for producing powder.

Example 19

15 g of *Smilacis glabra rhizoma*, 8 g of *Cichorii herba*, 10 g of *Plantaginis herba*, 18 g of *Coicis* semen, 8 g of *Pueraia lobata radix*, 4 g of *Alismatis rhizoma* and 2.0 g of tuna extract were weighed precisely.

The method for the preparation of the tuna extract includes taking and grinding the tuna, heating for 30 min at 80° C. as pretreatment, and enzymatic hydrolyzing at the temperature of 54° C. for a duration of 3.0 h. Protease which is preferably selected from the group consisting of acidic protease, papain, trypsin, proteolytic enzyme, neutral protease, flavourzyme and Alcalase protease was employed in the enzymatic hydrolysis in an amount of 0.5%-3.0% by weight of the pretreated tuna.

Next was the inactivation of the enzymes at the temperature of 96° C. for a duration of 20 min.

The supernatant was obtained by centrifugation, which was concentrated to a solids content of 38% at 0.08 MPa and 60° C. under vacuum and dried.

The raw materials described above were extracted twice, with the addition of water in an amount of 12 times at the first time, which was boiling extracted for 1.5 hours, and the addition of water in an amount of 8 times at the second time, which was boiling extracted for 1 hour, followed by the combination of the extracts from the above two extractions; the extracts were filtered at the temperature of 65° C. in a vacuum of −0.05 Mpa, and concentrated to a solids content of 20%; the granule products were obtained with the addition of auxiliaries according to the conventional process for producing granules.

Example 20 The Composition 29 g of *Smilacis glabra rhizoma*, 3 g of *Cichorii herba*, 3 g of *Plantaginis herba*, 3 g of *Coicis* semen, 1 g of *Alismatis rhizoma*, 5 g of tuna extract and 11 g of *Pueraia lobata radix* were weighed precisely.

The method for the preparation of the tuna extract includes taking and grinding the tuna, heating for 5 min at 80° C. as pretreatment, and enzymatic hydrolyzing at the temperature of 60° C. for a duration of 3.0 h. Acidic protease was employed in the enzymatic hydrolysis in an amount of 0.5% by weight of the pretreated tuna.

Next was the inactivation of the enzymes at the temperature of 100° C. for a duration of 10 min.

The supernatant was obtained by centrifugation, which was concentrated to a solids content of 45% at 0.08 MPa and 68° C. under vacuum and dried.

The raw materials described above were extracted twice, with the addition of water in an amount of 12 times at the first time which was boiling extracted for 1.5 hours, and the addition of water in an amount of 8 times at the second time, which was boiling extracted for 1 hour, followed by the combination of the extracts from the above two extractions; the extracts were filtered at the temperature of 65° C. in a vacuum of −0.08 Mpa, and concentrated to a solids content of 20%; the food products were obtained with the addition of auxiliaries according to the conventional process for producing food.

Example 21 The Composition 3 g of *Smilacis glabra rhizoma*, 16 g of *Cichorii herba*, 16 g of *Plantaginis herba*, 21 g of *Coicis* semen, 10 g of *Alismatis rhizoma*, 0.1 g of tuna extract and 3 g of *Pueraia lobata radix* were weighed precisely.

The method for the preparation of the tuna extract includes taking and grinding the tuna, heating for 30 min at 100° C. as pretreatment, and enzymatic hydrolyzing at the temperature of 50° C. for a duration of 9.0 h. Papain was employed in the enzymatic hydrolysis in an amount of 3.0% by weight of the pretreated tuna.

Next was the inactivation of the enzymes at the temperature of 90° C. for a duration of 20 min.

The supernatant was obtained by centrifugation, which is concentrated to a solids content of 30% at 0.03 MPa and 80° C. under vacuum and dried.

The raw materials described above were extracted twice, with the addition of water in an amount of 12 times at the first time which was boiling extracted for 1.5 hours, and the addition of water in an amount of 8 times at the second time, which was boiling extracted for 1 hour, followed by the combination of the extracts from the above two extractions; the extracts were filtered at the temperature of 85° C. in a vacuum of −0.03 Mpa, and concentrated to a solids content of 30%; the health products were obtained with the addition of auxiliaries according to the conventional process for producing health products.

Example 22

105 SPF grade SD rats, all of which are male and have a body weight of 200±20 (g), provided by Beijing Vital River Laboratory Animal Technology Co., Ltd. (license number: SCXK (Beijing) 2012-0001) were taken. Potassium oxonate, Jinan Chenghuishuangda Chemical Co., Ltd. product with the batch number of 12042001, was prepared with 0.1% CMC-Na into a suspension of a concentration of 0.15 g/ml in an amount for 3 d each time and the stock was stored at 4° C. Allopurinol, Tokyo chemical industry Co. Ltd. product with the batch number of MYRYA-IR, was prepared with 0.1% CMC-Na into a suspension of a concentration of 2.7 g/ml in an amount for 3 d each time and the stock was stored at 4° C. Uric acid and urea nitrogen test kit were provided by Centronic GmbH company in German, with the batch numbers of UF03121HH6G and UF01121GG66G respectively, and creatinine test kit was provided by Shanghai Lanyi Technology Co. Ltd. with the batch number of R102APA.

SD rats were adapted for 5 days in the experimental environment, and randomly divided by body weight into normal control group, model group, allopurinol group, Sample 1 (the composition of Chinese herbal medicines and tuna extract prepared in Example 18) high-dose group and low-dose group and Sample 2 (the composition of Chinese herbal medicines prepared in Example 18 excluding tuna extract) high-dose group and low-dose group. According to the clinical dose, the intragastric doses of Samples 1 and 2 were 5 times larger (0.2 ml/100 g) and 30 times larger (1.25 ml/100 g) than the recommended amount for human body for the low-dose groups and high-dose groups, respectively.

The same volume of drinking water was intragastrically administered to the normal control group every day, and the potassium oxonate was intragastrically administered to each of the rest groups of rats every morning at 1.5 g·kg$^{-1}$·d$^{-1}$; the same volume of physiological saline was intragastrically administered to the model group in the afternoon; the allopurinol was intragastrically administered to the allopurinol group at 27 mg·kg$^{-1}$·d$^{-1}$ in the afternoon; the samples to be tested of different doses diluted to the same volume were intragastrically administered to the Sample 1 of high-dose and low-dose groups and the Sample 2 of high-dose and low-dose groups in the afternoon.

Modeling principle: the rats were intragastrically administered with the chemical uricase inhibitor, potassium oxonate to inhibit the uricase activity in the rats, which make the uric acid in their body unable to be decomposed and resulting in an increase of serum uric acid to replicate the hyperuricemia model of rats.

TABLE 1

Scheme of grouping and administration

| Group | Number of Rats | Modeling Agents/Therapeutic Drugs/Health Food Sample 1 and 2 | Dose |
| --- | --- | --- | --- |
| Normal Control Group | 15 | — | Same volume of drinking water |
| Model Group | 15 | Potassium Oxonate | 1.5 g/kg |
| Model Group + Positive drug | 15 | Potassium Oxonate + Allopurinol | 1.5 g/kg + 27 mg/kg |
| Sample 1 Low-dose | 15 | Potassium Oxonate + Sample 1 | 1.5 g/kg + 2.1 ml/kg |
| Sample 1 High-dose | 15 | Potassium Oxonate + Sample 1 | 1.5 g/kg + 12.5 ml/kg |
| Sample 2 Low-dose | 15 | Potassium Oxonate + Sample 2 | 1.5 g/kg · d + 2.1 ml/kg |
| Sample 2 High-dose | 15 | Potassium Oxonate + Sample 2 | 1.5 g/kg + 12.5 ml/kg |

The body weights of the rats were monitored, the blood samples were collected to measure the uric acid, creatinine and urea nitrogen before the experiments and at the 15th day of the administration, and the variance ratio of the serum uric acid levels was measured and calculated.

Variance ratio of serum uric acid=(serum uric acid levels after the experiments−serum uric acid levels before the experiments)/serum uric acid levels before the experiments×100%.

The data was computed using SPSS 13.0 statistical software by one-way analysis of variance (ANOVA), the differences between two groups were compared by LSD test, and the results were expressed by mean±standard deviation ($\bar{x}$±s).

The analysis of variance was preceded by the test of the homogeneity of variance, and F value was calculated, F value<$F_{0.05}$ leads to the conclusion that the difference between the means of each group was not significant; if F value≤$F_{0.05}$ and P≥0.05, the statistical analysis was performed by pairwise comparisons between the means of a plurality of the experimental groups and the control group; the data of non-normality or of heterogeneity of variance were subject to appropriate variable conversion, and the statistical analysis was performed using the data converted which was able to meet the requirement of normality or homogeneity of variance; if the purpose of normality or homogeneity of variance was not achieved after the variable conversion, the rank-sum test was used instead for the statistical analysis.

In the comparison of the dose groups of the tested samples and the model group, positive results of the animal experiments on the function of the tested samples to reduce uric acid were confirmed by the reduction of serum uric acid value in any dose group with significant differences and the absence of marked increase in serum urea nitrogen and serum creatinine.

As shown in Table 2, the body weights of the animal gradually increase as the feeding time is prolonged, but no significant difference was observed when comparing the body weights of the animal of each groups after the experiments.

TABLE 2

The effect of the uric acid reducing health food on the animal body weights ($\bar{x}$ ± s) (Unit: g)

| Group | N | Before Experiments | 1 week after treatment | 2 weeks after treatment | 3 weeks after treatment | 4 weeks after treatment |
| --- | --- | --- | --- | --- | --- | --- |
| Normal Control Group | 15 | 286 ± 14 | 326 ± 20 | 354 ± 24 | 369 ± 27 | 392 ± 33 |
| Model Group | 15 | 291 ± 9 | 330 ± 12 | 360 ± 19 | 370 ± 26 | 400 ± 40 |
| Allopurinol Group | 15 | 290 ± 13 | 322 ± 20 | 352 ± 24 | 366 ± 28 | 387 ± 29 |
| Sample 1 Low-dose | 15 | 288 ± 14 | 317 ± 19 | 344 ± 22 | 358 ± 23 | 377 ± 26 |
| Sample 1 High-dose | 15 | 287 ± 12 | 319 ± 17 | 344 ± 24 | 361 ± 29 | 382 ± 29 |
| Sample 2 Low-dose | 15 | 288 ± 11 | 318 ± 15 | 347 ± 20 | 358 ± 23 | 380 ± 25 |
| Sample 2 High-dose | 15 | 288 ± 14 | 316 ± 24* | 342 ± 32* | 354 ± 36 | 373 ± 43 |

Note:
Compared with the model groups,
*P < 0.05

As shown in Table 2, animal body weights gradually increase as the feeding time is prolonged, but no significant difference is observed when comparing the animal body weights across the groups after the experiments.

As seen from Table 3, serum uric acid: the serum uric acid levels in the model groups are all increased significantly (P<0.001) compared to those in the normal control groups, and the serum uric acid levels in Sample 1 of high-dose and low-dose groups and Sample 2 of high-dose and low-dose groups are all decreased significantly (P<0.01 or P<0.001) compared to those in the model groups, wherein the serum uric acid level is decreased by 19% in Sample 1 of low-dose group, by 32% in Sample 1 of high-dose group, by 13% in Sample 2 of low-dose group and by 16% in Sample 2 of high-dose group, with the presence of dose-dependence to a certain degree after the intragastric administration of the same sample. The effects of reducing uric acid have no significant difference when comparing low dose of Sample 1 and Sample 2, while high dose of Sample 1 shows a better effect in lowering uric acid than of Sample 2 with a significant difference (P<0.05).

Urea nitrogen: the serum urea nitrogen levels in model groups are increased significantly (P<0.01 or P<0.001) compared to those in the normal control groups, and the serum urea nitrogen levels in Sample 1 of high-dose and low-dose groups and Sample 2 of high-dose and low-dose groups are all decreased significantly (P<0.01 or P<0.001) compared to those in the model groups, wherein the serum urea nitrogen level is decreased by 13% in Sample 1 of low-dose group, by 22% in Sample 1 of high-dose group, by 13% in Sample 2 of low-dose group and by 28% in Sample 2 of high-dose group, with the presence of dose-dependence to a certain degree after the intragastric administration of the same sample. There is no significant difference when comparing the same dose of Samples 1 and 2.

Creatinine: the serum creatinine levels in the model groups have no significant changes (P>0.05) compared to those in the normal control groups, and the serum creatinine levels in Sample 1 of high-dose group and Sample 2 of high-dose and low-dose groups are decreased significantly (P<0.05 or P<0.001) compared to those in the corresponding model group 2, wherein the serum creatinine level is decreased by 16% in Sample 1 of high-dose group, by 6% in Sample 2 of low-dose group and by 17% in Sample 2 of high-dose group, with the presence of dose-dependence to a certain degree after the intragastric administration of the same sample. The effect of reducing creatinine of Sample 2 in low dose is more significant (P<0.01) than that of Sample 1 in low dose.

in high dose was better than that of Sample 2 in high dose exhibiting a significant difference (P<0.05), which suggests that the tested Sample 1 (the composition of Chinese herbal medicines and tuna extract) has a superior effect than the Sample 2 (the composition of Chinese herbal medicines). A composition of the present invention having the function of lowering uric acid enables a variety of components to coordinate with each other in rational combinations by the formulation of Chinese herbal medicines and tuna extract, to achieve the healthcare function of reducing uric acid through multiple ways at multi-levels with significant effect of lowering uric acid.

Experiments implemented with the compositions prepared in Examples 1 to Example 17, and Example 19 to Example 21 of the present invention give the same or similar results as those with the composition prepared in Example 18, without significant differences (P>0.05).

A comprehensive analysis of the experimental results described above indicates that the compositions provided in the present invention have a significant effect of lowering uric acid (P<0.05).

Example 23 Comparative Test

Comparative Examples 1 to 5

The health food having the function of lowering uric acid provided in Comparative Example 1 of the present invention is prepared from the following components in parts by weight: *Coicis* semen 18, *Cichorii herba* 8, *Plantaginis herba* 8 and *Pueraia lobata radix* 8.

The health food having the function of lowering uric acid provided in Comparative Example 2 of the present invention is prepared from the following components in parts by weight: *Coicis* semen 18, *Motherwort* 10, *Cichorii herba* 8, *Plantaginis herba* 8, *Pueraia lobata radix* 8 and tuna extract 0.1.

The health food having the function of lowering uric acid provided in Comparative Example 3 of the present invention is prepared from the following components in parts by weight: *Coicis* semen 18, *Cassiae semen* 9, *Cichorii herba* 8, *Plantaginis herba* 8, *Pueraia lobata radix* 8 and tuna extract 0.5.

TABLE 3

The effect of intragastric administration of the uric acid lowering health care food for 15 d on the levels of uric acid, urea nitrogen and creatinine in animals ($\bar{x} \pm s$)

| Group | N | Uric Acid (μmol/L) | Urea Nitrogen (μmol/L) | Creatinine (μmol/L) |
|---|---|---|---|---|
| Normal Control Group | 15 | 133.8 ± 25.0 | 5.8 ± 0.8 | 29.3 ± 3.0 |
| Model Group | 14 | 256.4 ± 41.3*** | 6.7 ± 0.6** | 31.0 ± 3.3 |
| Allopurinol Group | 15 | 31.8 ± 10.3### | 6.2 ± 0.9 | 27.9 ± 2.2## |
| Sample 1 Low-dose | 15 | 207.8 ± 21.9### | 5.8 ± 0.9## | 31.5 ± 2.6 |
| Sample 1 High-dose | 15 | 173.2 ± 32.1### | 5.2 ± 0.8### | 26.1 ± 1.9### |
| Sample 2 Low-dose | 15 | 222.2 ± 19.6## | 5.8 ± 1.1## | 29.0 ± 2.9#ΔΔ |
| Sample 2 High-dose | 15 | 214.3 ± 41.0###▲ | 4.8 ± 0.7### | 25.8 ± 1.3### |

Note:
The model group compared with the normal control group, P < 0.01, *P < 0.001;
the health product sample group compared with the model group, #P < 0.05, ##P < 0.01;
ΔΔP < 0.01, Sample 1 of low-dose group compared with Sample 2 of low-dose group;
▲P < 0.05, Sample 1 of high-dose group compared with Sample 2 of high-dose group.

As can be seen from Table 1, 2, and 3, with the oral administration of the tested Sample 1 (the composition of Chinese herbal medicines and tuna extract) and Sample 2 (the composition of Chinese herbal medicines) for 15 d, the serum uric acid levels decreased remarkable (p<0.05) with statistical significance compared to those in the model group, which indicating that the test samples act to lowering uric acid. Also, the effect of lowering uric acid of Sample 1

The health food having the function of lowering uric acid provided in Comparative Example 4 of the present invention is prepared from the following components in parts by weight: *Coicis semen* 18, *Dioscorea rhizoma* 8, *Poria* 8 and tuna extract 0.5.

The health food having the function of lowering uric acid provided in Comparative Example 5 of the present invention is prepared from the following components in parts by weight: *Papaya* 6, *Dioscorea rhizoma* 8, *Poria* 8 and tuna extract 0.5.

Experimental group: Sample 1—the composition prepared in Example 1.

As seen from Table 6, the levels of uric acid, urea nitrogen and creatinine in the Comparative Examples 1 to 5 groups have no significant differences compared with those in the model group, suggesting that the comparative groups do not have the effect of lowering uric acid. However, Sample 1,

TABLE 4

Scheme of grouping and administration

| Group | Number of Rats | Modeling Agents/ Therapeutic Drugs/Health Food Sample 1/ Comparative Example 1 to 5 | Dose |
|---|---|---|---|
| Normal Control Group | 15 | — | Same Volume of Drinking Water |
| Model Group | 15 | Potassium Oxonate | 1.5 g/kg |
| Model Group + Positive drug | 15 | Potassium Oxonate + Allopurinol | 1.5 g/kg + 27 mg/kg |
| Sample 1 | 15 | Potassium Oxonate + Sample 1 | 1.5 g/kg + 12.5 ml/kg |
| Comparative Example 1 | 15 | Potassium Oxonate + Comparative Example 1 | 1.5 g/kg + 12.5 ml/kg |
| Comparative Example 2 | 15 | Potassium Oxonate + Comparative Example 2 | 1.5 g/kg + 12.5 ml/kg |
| Comparative Example 3 | 15 | Potassium Oxonate + Comparative Example 3 | 1.5 g/kg + 12.5 ml/kg |
| Comparative Example 4 | 15 | Potassium Oxonate + Comparative Example 4 | 1.5 g/kg + 12.5 ml/kg |
| Comparative Example 5 | 15 | Potassium Oxonate ++ Comparative Example 5 | 1.5 g/kg + 12.5 ml/kg |

TABLE 5

The effect of the uric acid reducing health food on animal body weights ($\bar{x} \pm s$) (Unit: g)

| Group | N | Before Experiments | 1 week after treatment | 2 weeks after treatment | 3 weeks after treatment | 4 weeks after treatment |
|---|---|---|---|---|---|---|
| Normal Control Group | 15 | 286 ± 14 | 326 ± 20 | 354 ± 24 | 369 ± 27 | 392 ± 33 |
| Model Group 2 | 15 | 291 ± 9 | 330 ± 12 | 360 ± 19 | 370 ± 26 | 400 ± 40 |
| Allopurinol Group | 15 | 290 ± 13 | 322 ± 20 | 352 ± 24 | 366 ± 28 | 387 ± 29 |
| Sample 1 | 15 | 287 ± 12 | 319 ± 17 | 344 ± 24 | 361 ± 29 | 382 ± 29 |
| Comparative Example 1 | 15 | 292 ± 10 | 322 ± 17 | 345 ± 30 | 365 ± 34 | 385 ± 40 |
| Comparative Example 2 | 15 | 286 ± 12 | 325 ± 22 | 355 ± 23 | 371 ± 29 | 389 ± 42 |
| Comparative Example 3 | 15 | 288 ± 11 | 325 ± 16 | 354 ± 24 | 367 ± 29 | 387 ± 39 |
| Comparative Example 4 | 15 | 290 ± 10 | 327 ± 15 | 367 ± 30 | 373 ± 32 | 390 ± 35 |
| Comparative Example 5 | 15 | 287 ± 13 | 323 ± 20 | 362 ± 34 | 372 ± 36 | 387 ± 43 |

Note:
Compared with the model groups,
* $P < 0.05$

As shown in Table 5, the body weights of the animal gradually increase as the feeding time is prolonged, and no significant differences are observed when comparing the animal body weights across the groups at the time of their measurements by weighing every week.

i.e. the composition prepared in Example 1 of the present invention was able to lower uric acid significantly ($P<0.05$).

Experiments implemented using the compositions prepared in Examples 2 to Example 21 of the present invention

TABLE 6

The effect of intragastric administration of the uric acid reducing health food for 15 d on the levels of uric acid, urea nitrogen and creatinine in the animals ($\bar{x} \pm s$).

| Group | N | Uric Acid (μmol/L) | Urea Nitrogen (μmol/L) | Creatinine (μmol/L) |
|---|---|---|---|---|
| Normal Control Group | 15 | 133.8 ± 25.0 | 5.8 ± 0.8 | 29.3 ± 3.0 |
| Model Group | 14 | 256.4 ± 41.3*** | 6.7 ± 0.6** | 31.0 ± 3.3 |
| Allopurinol Group | 15 | 31.8 ± 10.3### | 6.2 ± 0.9 | 27.9 ± 2.2## |
| Sample 1 | 15 | 173.2 ± 32.1### | 5.2 ± 0.8### | 26.1 ± 1.9### |
| Comparative Example 1 | 15 | 253.2 ± 50.1 | 6.5 ± 0.8 | 29.1 ± 3.3 |
| Comparative Example 2 | 15 | 249.7 ± 45.7 | 6.3 ± 0.6 | 32.1 ± 2.9 |
| Comparative Example 3 | 15 | 213.4 ± 48.1 | 6.2 ± 0.7 | 30.9 ± 3.5 |
| Comparative Example 4 | 15 | 225.2 ± 45.7 | 6.2 ± 1.1 | 29.5 ± 3.1 |
| Comparative Example 5 | 15 | 212..3 ± 51.0 | 6.1 ± 0.7 | 29.8 ± 2.3 |

Note:
The model group compared with the normal control group, $P < 0.01$, *$P < 0.001$;
the sample group compared with the model group, #$P < 0.05$, ##$P < 0.01$;

give the same or similar results as those using the composition prepared in Example 18, without significant differences ($P>0.05$).

A comprehensive analysis of the experimental results described above indicates that the compositions provided in the present invention have a significant effect of lowering uric acid ($P<0.05$).

The above description gives only the preferred embodiments of the present invention, and it should be noted that for those of ordinary skill in the art, a number of improvements and modifications can be made without departing from the principle of the invention, which are also regarded as falling into the scope claimed in the present invention.

What is claimed is:

1. A composition comprising *Smilacis glabra rhizoma* in an amount of 3 to 29 parts by weight, *Cichorii herba* in an amount of 3 to 16 parts by weight, *Plantaginis herba* in an amount of 3 to 16 parts by weight, *Coicis* semen in an amount of 3 to 21 parts by weight, *Alismatis rhizoma* in an amount of 1 to 10 parts, Tuna in an amount of 0.1 to 5 parts by weight, and *Pueraia lobata radix* in an amount of 3 to 11 parts by weight, and wherein the composition is in the form of a tablet, capsule or pill.

2. A method of reducing uric acid in a subject in need thereof, comprising administering an effective amount of the composition of claim 1 to said subject.

* * * * *